United States Patent [19]

Weir et al.

[11] Patent Number: 5,665,866

[45] Date of Patent: Sep. 9, 1997

[54] PROCESS FOR OBTAINING ANTIBODIES UTILIZING HEAT TREATMENT

[75] Inventors: Andrew Neil Charles Weir, Maidenhead; Neil Andrew Bailey, Cheltenham, both of United Kingdom

[73] Assignee: Celltech Therapeutics Limited, Berkshire, United Kingdom

[21] Appl. No.: 367,313

[22] PCT Filed: Jul. 22, 1993

[86] PCT No.: PCT/GB93/01548

§ 371 Date: Mar. 14, 1995

§ 102(e) Date: Mar. 14, 1995

[87] PCT Pub. No.: WO94/02608

PCT Pub. Date: Feb. 3, 1994

[30] Foreign Application Priority Data

Jul. 22, 1992 [GB] United Kingdom ............... 9215540

[51] Int. Cl.⁶ .................... C12P 21/08; C07K 16/00; C12N 15/13; C12N 15/69
[52] U.S. Cl. .................. 530/390.5; 530/387.1; 530/387.3; 435/69.6; 435/71.1; 435/173.8; 435/252.3
[58] Field of Search ................ 424/133.1; 435/69.1, 435/69.6, 71.1, 173.8, 252.3; 530/387.1, 387.3, 390.5

[56] References Cited

U.S. PATENT DOCUMENTS 5,015,573  5/1991  Yarranton et al. ................. 435/69.1

FOREIGN PATENT DOCUMENTS

| 0003062 | 7/1979 | European Pat. Off. . |
| 0105554 | 4/1984 | European Pat. Off. . |
| 0109150 | 5/1984 | European Pat. Off. . |
| 0121386 | 10/1984 | European Pat. Off. . |
| 89/02465 | 3/1989 | WIPO . |
| 92/01059 | 1/1992 | WIPO . |
| 94/02607 | 2/1994 | WIPO . |
| 94/13805 | 6/1994 | WIPO . |

OTHER PUBLICATIONS

Cabilly, "Growth at sub-optimal temperatures allows the production of functional, antigen-binding Fab fragments in *Escherichia coli*", Gene, vol. 85, pp. 553–557, 1989.

Schein et al., "Formation of soluble recombinant proteins in *Escherichia coli* is favored by lower growth temperature", Bio/Technology, vol. 6, pp. 291–294, 1988.

Wright et al., "Dual-origin plasmids containing an amplifiable ColE1 ori; temperature-controlled expression of cloned genes", Gene, vol. 49, pp. 311–321, 1986.

Roberts et al., "Generation of an antibody with enhanced affinity and specificity for its antigen by protein engineering", Nature, vol. 328, pp. 731–734, 1987.

Chalmers et al., "Effects of Temperature on *Escheichia coli* Overproducing β-Lactamase or Human Epidermal Growth Factor", Appl. Environ. Microbiol., vol. 56, pp. 104–111, 1990.

Primary Examiner—Marian C. Knode
Assistant Examiner—Nancy A. Johnson
Attorney, Agent, or Firm—Foley & Lardner

[57] ABSTRACT

This invention relates to a process for obtaining antibodies in soluble and correctly folded and assembled form. It comprises a step to raise the temperature at a time in the process selected to facilitate the subsequent isolation of soluble, correctly folded and assembled antibody, substantially free of other antibody-related material. The operating temperature may be raised at any stage in the microbial fermentation or eukaryotic cell culture, or at any stage during extraction and purification of the antibodies.

12 Claims, 14 Drawing Sheets

FIG.1
DUAL ORIGIN PLASMIDS
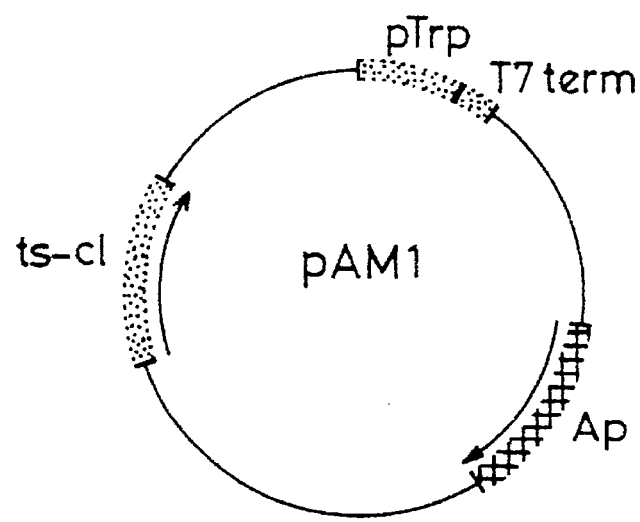
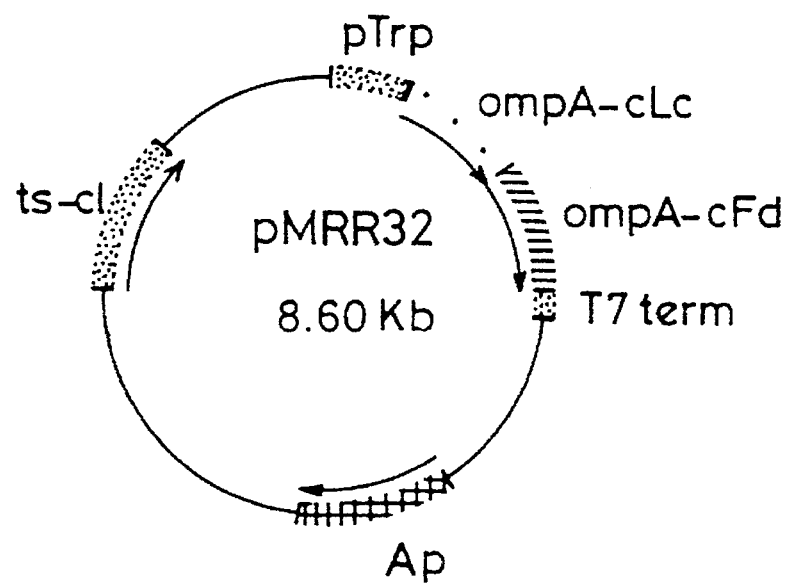

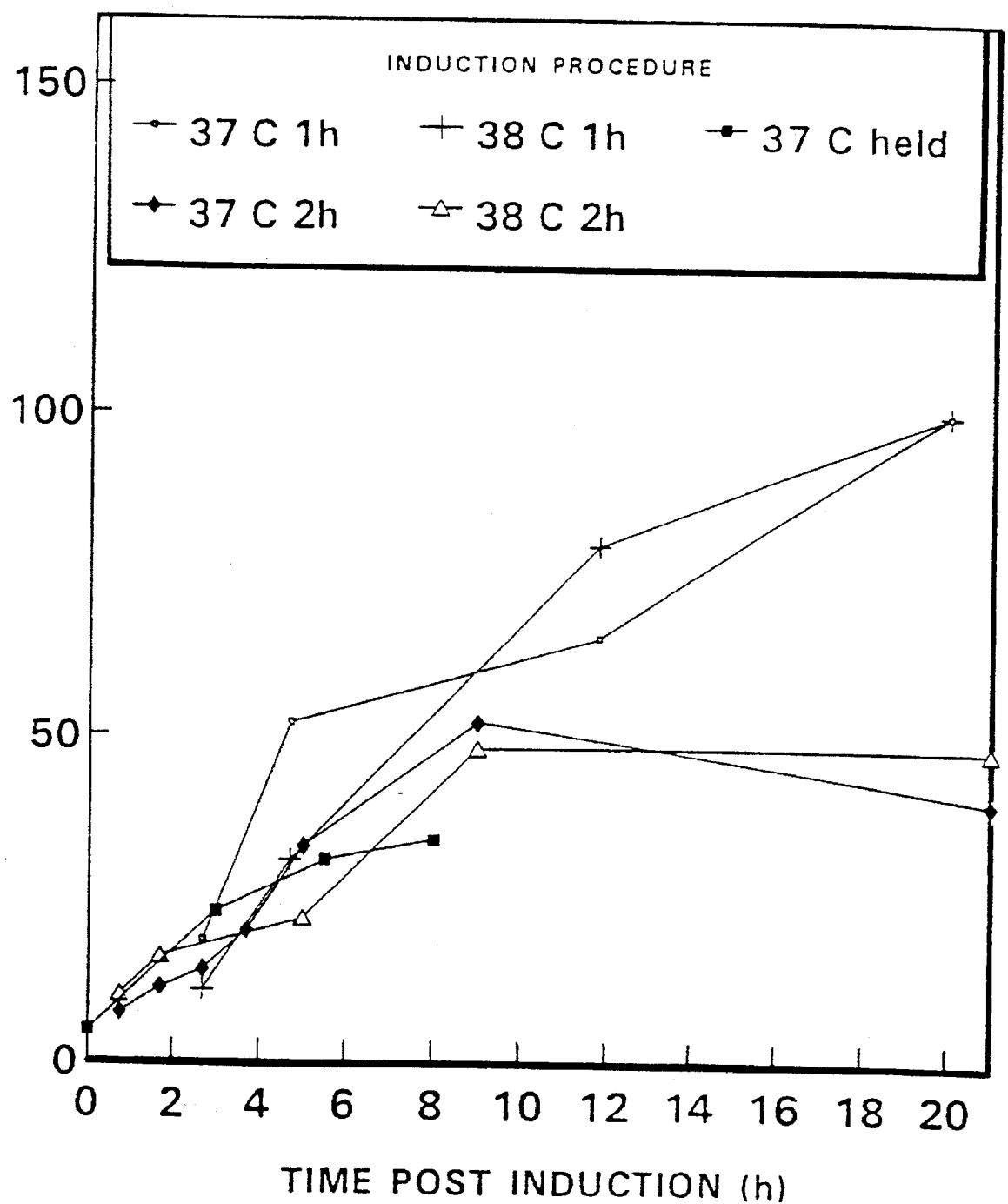

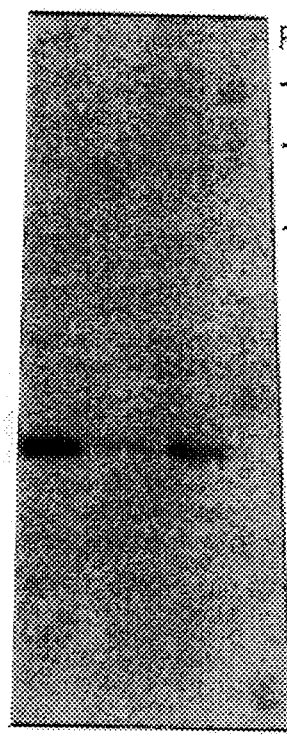
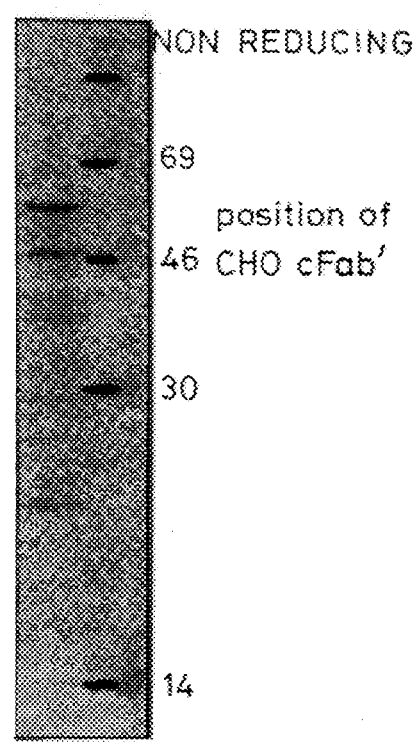

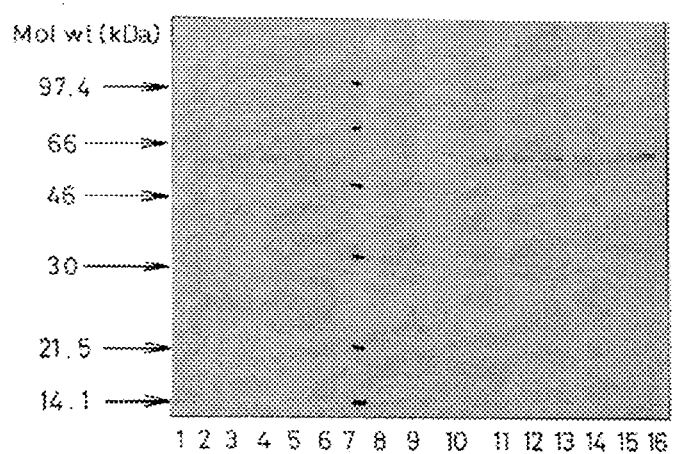

FIG.10
NON-REDUCED WESTERN BLOT
OF 30°C AND 46°C EXTRACTIONS
ON FERMENTATION CELLS

Non-reduced Western blot of extractions performed in Tris/EDTA at 30°C and 46°C on cell samples taken over the course of a fermentation from induction to harvest.

Lane 1:   30oC - Preinduction Cells
Lane 2-6: 30oC extraction on samples taken 8.3, 9.3, 13.5, 14.8 and 20.8 hours after induction
Lane 7:   Molecular Weight Markers
Lane 8:   46oC - Preinduction Cells
Lane 9-16: 46oC extractions on samples taken 2, 4.8, 5.8, 8.3, 9.3, 13.5, 14.8 and 20.8 hours after extraction

FIG. 12a  FIG. 12b
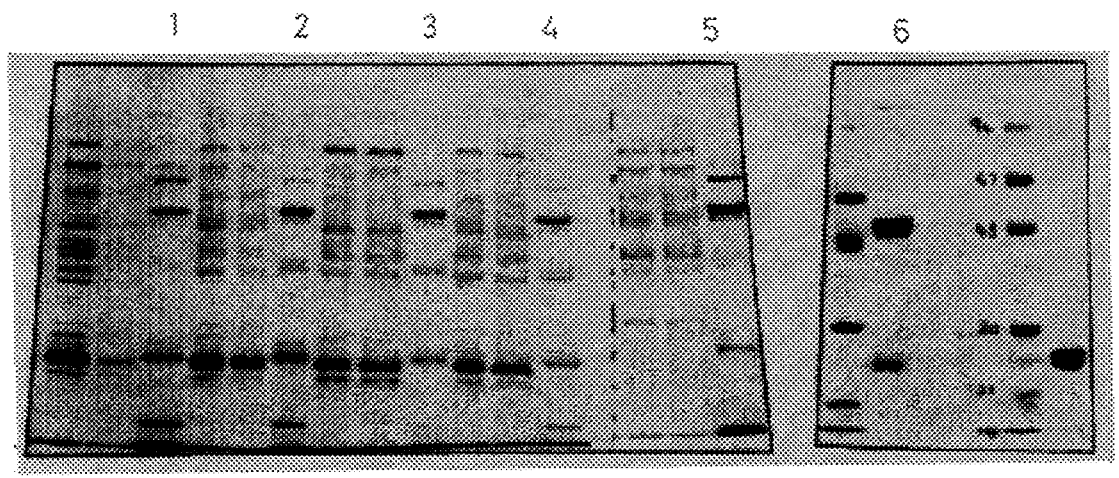

PROCESS FOR OBTAINING ANTIBODIES UTILIZING HEAT TREATMENT

FIELD OF THE INVENTION

This invention provides an improvement to a process for obtaining antibodies in soluble, correctly folded and assembled form.

DESCRIPTION OF BACKGROUND ART

The rapid developments in recombinant DNA techniques have resulted in the identification and isolation of many novel genes, some of known function and some of unknown function. Invariably there is a need to express the gene in a heterologous cell system in order to produce material for structure-function studies, diagnostic reagents such as monoclonal or polyclonal antibodies and material for in vivo activity testing and therapy.

Several alternative systems for the expression of foreign genes have been developed including systems based upon mammalian cells, insect cells, fungal cells, bacterial cells and transgenic animals or plants. The choice of expression system for a given gene depends upon the likely features of the encoded protein, for example any post-translational protein modifications needed for biological activity, as well as the objective of the study. Other important considerations for the investigator are the facilities available and the time and cost involved in generating the amounts of recombinant protein required.

The most widely used and convenient system for the production of foreign proteins remains that based on the prokaryote Escherichia coli. The advantages of this system comprise the ease of gene manipulation, the availability of reagents including gene expression vectors, the ease of producing quantities of protein (up to a gramme in simple shake-flask culture), speed and the high adaptability of the system to express a wide variety of proteins.

Expression of any foreign gene in E. coli begins with the insertion of a cDNA copy of the gene into an expression vector. Many forms of expression vector are available. Such vectors usually comprise a plasmid origin of DNA replication, an antibiotic selectable marker and a promoter and transcriptional terminator separated by a multi-cloning site (expression cassette) and a DNA sequence encoding a ribosome binding site. The method of transcriptional regulation varies between the various promoters now available (ptac, λpL, T7). The ptac and T7 expression based systems are controlled by the chemical inducer IPTG, whilst the λ promoters are controlled by a temperature switch.

A problem encountered with E. coli based expression systems is the difficulty of producing material which is acceptable for therapeutic use. The use of complex media, antibiotic selection and potentially hazardous inducers such as IPTG may potentially render products such as recombinant antibody fragments produced by E. coli fermentation technology unacceptable to the regulatory authorities for clinical applications. Evidence demonstrating clearance of these agents from the final product must be provided in order to secure regulatory approval. Clearance of these agents, and especially demonstrating such clearance, is expensive. It is therefore desirable that an expression system should avoid the three above-mentioned problems.

A further problem is that proteins produced in bacterial cells are often precipitated as insoluble aggregates within the bacterial cell. This problem has been addressed in a number of ways in the prior art. For example, a large number of patent specifications teach solubilisation of aggregates by the use of chaotropic denaturants and subsequent renaturation. These procedures involve the use of expensive denaturing chemicals, are time-consuming and introduce chemical agents into the production process of which clearance demonstration will be required by the regulatory authorities if the product is destined for clinical use.

An alternative approach has involved attempting to secrete the heterologous protein from the bacteria into the culture medium.

A number of recent advances have been made in bacterial protein expression, both relating to secretion and non-secretion systems. It has been observed, by a number of groups working in this field, that expression of soluble protein products is favoured by culturing the bacteria at 30° C. or below.

For example, Cabilly (Gene, 85, p. 553–557, 1989) observed that expression of the Fd' fragment of an antibody directed against carcinoembryonic antigen (CEA) was improved at lower temperatures. This leads to a higher quantity of soluble heavy chain being recovered form the bacteria after lysis of the cells. The Fd' fragment was expressed with a complementary κ light chain fragment in order to allow the formation of Fab fragments. A greater yield of active, soluble Fab fragments was obtained at 21° C. and 30° C. than at 37° C.

Schein and Noteborn, Bio/Technology 6, p. 291–294, 1988, analysed the expression of three proteins, human interferon-α2 (IFN-α2), human interferon-γ (IFN-γ) and murine Mx protein at 37° C. and at 23°–30° C. It was observed that proteins recovered from cell lysates were insoluble when the bacteria were grown at 37° C. However, solubility was greatly increased by expression at 30° C. The formation of insoluble protein is due to the aggregation of the heterologous polypeptide into inclusion bodies, a result of incorrect folding of the polypeptide chain.

The effect of temperature on proteins produced by secretion systems has been shown to be similar. Chalmers et al, in Applied and Environmental Microbiology, 56 (1), p. 104–111, 1990, demonstrated that both human interferon and β-lactamase, both secreted proteins, produced in bacterial-cell culture were both more abundantly produced at 20° C. than at 37° C. Furthermore, the incidence of inclusion bodies was reduced at the lower temperature.

Chalmers et al conclude that for commercial production, as exemplified by chemostat experiments, culture at lower temperatures leads to more soluble proteins being produced.

Antibodies and antibody fragments, especially chimeric, recombinant or humanised derivatives thereof, are a class of proteins which it would be extremely desirable to be able to produce by recombinant DNA technology. By humanised antibodies, it is intended to refer to antibodies in which the constant regions are derived from human immunoglobulins, while at least the complementarity determining regions (CDRs) of the variable domains are derived from murine monoclonal immunoglobulins.

A number of improvements over natural immunoglobulins have been documented in the literature, which can only be put into practice by recombinant DNA technology. For instance, the production of CDR-grafted antibodies having CDRs from murine antibodies coupled to human framework regions can only be undertaken using a recombinant expression system. Furthermore, such systems are extremely useful for the production of antibody fragments which are not readily obtained by proteolytic cleavage, such as Fv fragments, and antibody fusions comprising an effector or reporter molecule attached to the antigen binding molecule.

Recombinant antibody fragments, whether they be entire antibodies, Fab, Fab', F(ab')$_2$ or Fv fragments, consist of heavy and light chain dimers. A recombinant expression system should therefore be capable of expressing both heavy and light chain genes in such a manner as to render the individual peptides capable of self-assembly into the final product. This has been a stumbling block for recombinant antibody production, and indeed attempts have been made to solve the problem. An example of this is the production of "single chain" Fv fragments, wherein the heavy and light chain polypeptides are physically joined together by a flexible linker group. These molecules avoid the problems of chain association between free heavy and light chain polypeptides.

This system is not necessary, however, for the production of larger antibody fragments such as Fabs, which comprise heavy and light constant region chains as well as heavy and light variable region chains. These fragments are large enough not to require coupling through a linker. For such applications it is desirable to express heavy and light chains separately in the same cell.

In order to facilitate correct assembly of heavy and light chains of antibody fragments, it is preferable to employ an expression system in which the chains are secreted into the periplasm of the host cell or into the culture medium rather than precipitated into the cell as inclusion bodies.

Dual Origin vectors (DUOV), for example as described in our U.S. Pat. No. 5,015,573, have been found to be particularly suitable for expressing antibody fragments. This has been shown to be the case, particularly when used in combination with protease-deficient bacterial host cells (see our International Patent Specification WO89/02465). The dual origin vector pAM1, (Wright et al., Gene, 49, p. 311, 1986), which comprises both pSC101 and colE1 replication functions, replicates at low copy number using the pSC101 replication functions at 30° C. At this temperature, the colE1 replication functions, under the control of the λ pR promoter, are tightly controlled by the cI857 repressor. Any foreign DNA inserted into the expression site of pAM1 is transcriptionally controlled by this being placed under the influence of the trp promoter, which is regulated by the host chromosomal trpR repressor.

The cI857 repressor is temperature sensitive, therefore increasing the temperature of the growth medium above 34° C. leads to deregulation of the colE1 replication functions and increase in copy number from about 5 per cell to several hundred per cell. This causes the host trpR repressor to be titrated out, and transcription of foreign DNA from the trp promoter can take place.

However, secretion of antibody fragments from host cells transformed with DUOV vectors has not previously been attempted. In International Patent Specification WO89/02465 we describe a process for the expression of antibody fragments using DUOV vectors. However, the antibody fragments are expressed intracellularly and are precipitated as insoluble aggregates. These aggregates need to be solubilised by the use of chaotropic denaturants and/or other solubilisation techniques.

SUMMARY OF THE INVENTION

Accordingly, it is an object of the present invention to provide a process for obtaining antibodies in soluble, correctly folded and assembled form. When antibody molecules are expressed in bacterial cells transformed with a vector comprising DNA coding for said antibodies we have found that SDS PAGE analysis of material secreted and exported into the medium, material recovered from the periplasm and purified material from either source, consists of four principal bands representing correctly folded and assembled antibody; partially degraded fragments thereof, and free heavy and light chain. We have now found that by introducing an elevated temperature step it is possible to obtain soluble, correctly folded and assembled antibody as revealed by the presence of a single band on SDS PAGE.

According to the invention, therefore, there is provided an improvement to a process for obtaining antibodies in soluble, correctly folded and assembled form substantially free of other antibody related material said improvement comprising the use in the process of a step to raise the operating temperature to an elevated temperature at a time in the process selected to facilitate the subsequent isolation of soluble, correctly folded and assembled antibody substantially free of other antibody related material.

Antibody which is 'correctly folded and assembled' is shown by the presence of a single band corresponding to the expected molecular weight for assembled heavy and light chains on non-reducing SDS PAGE.

Other antibody related material will typically be free heavy and light chain or a part thereof, partially degraded fragments of correctly folded and assembled antibody.

The process of the invention may be used for selectively isolating antibodies in soluble, correctly folded and assembled form from microbial cell cultures or eukaryotic cell cultures.

The elevated temperature step may be introduced at any stage in the process for the production or isolation of antibodies, especially recombinant antibodies. For example, the heat treatment may be carried out at some stage during the expression phase of a fermentation or cell culture of a host cell transformed with at least one vector comprising at least one heterologous DNA sequence coding for all or part of an antibody heavy and/or light chain, or some other stage of a fermentation or cell culture, or during the extraction and purification of the antibodies from the fermentation or cell culture. It may be carried out by heat treating the whole cells isolated from the fermentation or cell culture; by heat treating a homogenate of the whole cells; or by introducing a heat treatment stage during the process of extraction and purification of the antibodies from the fermentation or cell culture.

In a preferred embodiment the invention provides a process for selectively obtaining antibodies in soluble, correctly folded and assembled form wherein the operating temperature is raised to an elevated temperature step during the extraction and purification of the antibodies from a microbial cell culture or eukaryotic cell culture.

In a particularly preferred embodiment the invention provides a process for selectively obtaining antibodies in correctly folded and assembled form from a solution containing a mixture of correctly folded and assembled antibody and other antibody related material comprising the steps of 1. heating the said solution and 2. isolating the correctly folded and assembled antibody from the heated solution.

The correctly folded and assembled antibody may be isolated using conventional techniques such as for example by homogenisation; clarification by filtration of centrifugation; precipitation, e.g. by treatment with ammonium sulphate, polyethylene glycol or caprylic acid; affinity chromatography e.g. protein-A, protein-G, antigen-affinity or anti-IgG affinity chromatography; ion-exchange chromatography e.g. DEAE or hydroxyapatite; hydrophobic interaction chromatography or by gel filtration. Methods for isolating and purifying antibodies are further described in "Antibodies: A Laboratory Manual"; Ed Harlow, and David Lane, published by Cold Spring Harbor Laboratories 1988.

These techniques may be used individually or in combination as appropriate depending on which stage in the process the operating temperature is raised to the elevated temperature.

The operating temperature is raised to an elevated temperature preferably at a stage in the extraction purification process prior to the removal of cells or cell debris. We believe that the cells or cell debris assist in the removal of partially degraded and incorrectly folded antibodies for example during centrifugation.

Where the heat treatment step is carried out at the last stage in the purification of the antibody it is desirable to mimic the cell and cell debris effect by providing a hydrophobic surface for denatured and/or incorrectly assembled antibodies to attach. The hydrophobic surface may for example be provided by using a batch hydrophobic chromatography matrix, and adding this to the reaction mixture prior to heat treatment. Examples of such batch hydrophobic chromatography matrices am well known in the art and include $C_{18}$ alkyl chains linked to a support matrix such as sepharose, agarose, or silica e.g. butyl sepharose, phenyl sepharose or octyl sepharose; or polymers such as cellulose or polystyrene.

In a particularly preferred embodiment the invention provides a process for obtaining antibodies in correctly folded and assembled form from a solution containing a mixture of correctly folded and assembled antibody and other antibody related material comprising the steps of 1. heating the said solution in the presence of batch hydrophobic chromatography matrix material and 2. isolating the correctly folded and assembled antibody from the heated solution.

The solution will most conveniently be a partially purified solution, which may be for example heat treated at 40°–46° C. for 10–14 hours.

In a preferred embodiment, a homogenate of whole cells is heat treated at 46° C. for 18 h prior to extraction and purification of the antibody.

The solution of antibody may for example be in a buffered solution using buffer salts such as Tris, acetate or phosphate. The pH of the antibody solution may, for example be from pH2 to pH10 and will most especially be around neutral pH i.e. pH6–pH8. The ionic strength of the solution of antibody may be varied using chaotropic salts such as ammonium sulphate or sodium sulphate. The solution of antibody may also be a pure aqueous solution with no added solutes or an aqueous solution of a polar organic solvent such as an alcohol e.g. ethanol.

The process according to the invention preferably selectively isolates antibody molecules in soluble, correctly folded and assembled form.

Suitable examples of microbial host cells include bacteria such as gram positive bacteria or gram negative bacteria e.g. E. coli such as E. coli K12 strain W3110 or XL1 Blue or, yeast cells such as S. cerevisiae cells, and examples of eukaryotic cells include for example mammalian cells such as CHO cells and myeloma or hybridoma cell lines, for example, NSO cells.

Where the operating temperature is raised to an elevated temperature at some stage during the expression phase or some other stage of the fermentation or cell culture, heat treatment is preferably carried out for a prolonged time. It may be, for example, for greater than 10 h, more preferably greater than 14 h and most preferably from 18–24 h.

Where the operating temperature is raised to an elevated temperature step during the extraction and purification of the antibodies from the fermentation or cell culture, this may be carried out for shorter time periods. For example, a solution containing a mixture of correctly folded and assembled antibody and other antibody related material may be flash treated at high temperatures or heat treated for up to 24 h, preferably for 10–18 h most preferably 12 h.

As used herein the term 'elevated temperature' denotes temperatures within the range 34° C. to 60° C., more preferably 37° C. to 48° C. and is most preferably 45° C. or 46° C.

We have found that the process of the invention unexpectedly provides an efficient and convenient way of selecting out soluble, correctly folded and assembled antibody.

The elevated temperature step may be introduced at the expression phase of a fermentation or cell culture.

According to one embodiment of the process of the present invention, there is further provided a process for obtaining antibody molecules in soluble, correctly folded and assembled form from bacterial cell culture comprising the steps of:

a) culturing a bacterial cell transformed with at least one expression vector comprising a secretion signal sequence, an origin of replication which is inducible from a repressed state at a repressive temperature, at which it replicates at a low copy number, to an induced state at an elevated permissive temperature, at which it replicates at a high copy number, and a DNA coding sequence encoding all or part of an antibody molecule comprising a light chain polypeptide and a heavy chain polypeptide under the control of a promoter which is repressed when the vector is at a low copy number and of a secretion sequence, in a medium at the repressive temperature at which the vector is maintained at a low copy number and recombinant gene expression is not induced;

b) raising the operating temperature of the culture medium to the elevated permissive temperature to induce replication of the vector to high copy number;

c) maintaining the operating temperature of the medium at the elevated permissive temperature; and d) optionally collecting the antibody molecule product expressed into the periplasm of the host cell or the culture medium.

It has now been found, surprisingly, that although a greater quantity of protein may be expressed and secreted from the host cell at the restrictive temperature, a greater proportion of this protein is soluble and correctly folded and assembled if the expression is carried out at the elevated permissive temperature.

The restrictive temperature is preferably within the range of 10° to 33° C., while the elevated permissive temperature is within the range of 34° to 45° C. Advantageously, the restrictive temperature is 30° C. and the elevated permissive temperature is 37° C.

The inducible vector system for use in the present invention may be a vector system in which vector copy number and expression of heterologous gene(s) is inducible by variation of the temperature at which the host is cultured. For example, the expression system may comprise a runaway replication vector of the type described in British Patent Specification GB-B-557774.

Preferably, however, the expression system comprises a dual origin vector, for example as described in our British Patent Specification GB-A-2136814 or our U.S. Pat. No. 5,015,573. A dual origin vector is a vector comprising two replication systems; a first origin of replication resulting in a low copy number and stable inheritance of the vector, and a second, high copy number origin of replication at which replication is directly controllable as a result of replacement of or alteration by DNA manipulation of the natural vector sequences which control replication at said second origin.

The use of dual origin vectors has been found to be particularly advantageous for the expression of antibody products, due to the enhanced stability of the vectors.

A novel induction system which provides tightly regulated expression with medium to low copy number vectors in defined media which maintains plasmid stability and allows the host cells to be cultured in the absence of antibiotic selection is described in our copending International patent application filed on even date herewith and derived from British patent application number 9215550.6 filed 22nd Jul. 1992. This induction system is as follows: a host cell transformed with a vector comprising a coding sequence under the control of an inducible promoter which is repressed by a mature endogenous cellular repressor in defined medium is cultured under conditions such that the inducible promoter is repressed, and expression of the heterologous protein is induced by increasing the metabolic rate of the host cell thereby depleting the levels of the mature endogenous cellular repressor. The increase in metabolic rate is preferably brought about by switching the carbon source, such as from glycerol to glucose.

The use of particularly stable expression vectors in defined medium in the absence of antibiotic selection is described in our copending International patent application filed on even date herewith and derived from British patent application number 9215541.5 filed 22nd Jul. 1992. These stable expression vectors comprise one or more heterologous DNA sequences under the control of a regulatable promoter, an origin of replication and a transcriptional terminator.

The process for obtaining a soluble, correctly folded and assembled antibody described herein may be used in conjunction with the process of either or both of the above mentioned patent applications.

A vector for use in producing antibody molecules preferably comprises heavy chain and light chain genes arranged with the light chain gene located closer to the promoter such that it is transcribed first. It has been observed that placing the light chain gene closer to the promoter, in such a manner that it is translationally coupled to the gene which the promoter is directly coupled to, and placing the heavy chain gene downstream from the light chain gene in such a manner that it does not benefit from translational coupling, both cell viability and efficiency of antibody secretion are enhanced.

In order to effect translational coupling, the natural coding sequence of the bacterial gene whose promoter is being used in the expression vector is altered in order to introduce a stop codon just before the beginning of the sequence of the inserted heterologous gene. It is hypothesized that this causes ribosomes, which are efficiently assembled on the mRNA of the bacterial coding sequence, to become disengaged in the close proximity of the translational start site of the heterologous mRNA. This favours the reassembly of the ribosomes on the heterologous mRNA, thus increasing the level of expression.

It is postulated that expression of an excess of heavy chains is deleterious to the host cell. However, arranging the light chain gene such that expression of light chain is favoured ensures an excess of light chains in the cell, thus avoiding the problems associated with excess heavy chain production. The arrangement of cistrons described is designed to favour the expression of an excess of light chains.

In a preferred embodiment of the vector for use in the invention, secretion of both heavy and light chain genes is directed by E. coli ompA signal sequences. Preferably, the ompA translation initiation signals are also included.

Advantageously, the ompA-antibody light chain fusion is translationally coupled to the lacZ peptide translated from the tac promoter. This may require the alteration of the ompA translation initiation sequence to introduce a stop codon.

Advantageously, the culture medium used in the method of the invention is a chemically defined medium. This allows the formulation of a process the product of which is acceptable to the regulatory authorities, which is highly desirable in the case of recombinant antibody products.

Examples of chemically defined medium are provided in Pirt S. J. (1975) "Principles of Microbe and Cell Cultivation", Blackwell Scientific Publications.

Preferably, the-defined medium used in the method of the invention does not contain antibiotic. It has been found that the dual origin vectors used in the method of the invention are stable in the absence of antibiotic selection. The stability of the plasmids is further improved by favouring the expression of light chain, as described above.

In a further aspect the invention provides an antibody composition comprising soluble, correctly folded and assembled antibody substantially free of other antibody related material.

As used herein the term 'substantially free of other antibody related material' denotes that the correctly folded and assembled form of the antibody will be in excess of 90% more usually in excess of 95%, of other antibody related material.

In a preferred embodiment of this aspect of the invention the antibody is a recombinant antibody or fragment thereof.

The antibody molecules may comprise natural antibody molecules, chimeric antibody molecules (the variable domains derived from one species and class of antibody and remaining Ig sequences derived from another species or class of Ig), altered antibody molecules (variable Ig domains plus an additional polypeptide sequence having a different, non-Ig function, such as an enzyme or toxin), humanised antibody molecules and engineered antibody molecules (wherein the Ig amino acid sequence has been altered from the natural sequence, e.g. by site-directed mutagenesis, with a view to altering a characteristic of the molecule, e.g. antigen binding specificity or affinity, for example as described in Roberts et al., Nature, 238, 731–734, 1987). The antibody molecules may comprise suitable combinations of the above types of antibody molecule.

Preferably, the antibody molecule is a humanised antibody molecule comprising at least the CDRs of a non-human antibody attached to the framework of a human antibody.

More preferably, the antibody molecule is an antibody fragment. For example, the antibody molecule may be a Fab, Fab', (Fab')$_2$ or Fv fragment. Advantageously, it is a Fab or Fab' fragment.

The antibody molecules may have any desired antigen specificity. For example, the antibody molecules may have specificity for a cell-specific antigen, such as a tumour antigen, T cell marker, etc. Particularly preferred are antibody molecules which have specificity for tumour-associated antigens such as CEA and TAG72. Chimeric A5B7 antibodies and antibody fragments are described in our copending International patent application WO 92/01059.

Also preferred are antibodies having specificity for the epitope recognised by murine monoclonal antibody A33 as described in our copending British patent application number 9225853.2 filed 10th Dec. 1992. Particularly preferred are humanised and chimeric forms of A33, and most particularly preferred are Fab' fragments thereof.

The antibodies may be site-specific antibodies such as tumour-specific or cell surface-specific antibodies, suitable for use in in vivo therapy or diagnosis, e.g. tumour imaging. Examples of cell surface-specific antibodies are anti-T cell-antibodies, such as anti-CD3, and CD4 and adhesion molecules, such as CR3, ICAM and ELAM. The antibodies may have specificity for interleukins (including lymphokines, growth factors and stimulating factors), hormones and other biologically active compounds, and receptors for any of these. For example, the antibodies may have specificity for any of the following: Interferons α, β, γ or δ, IL1, IL2, IL3 or IL4, etc., TNF, GCSF, GMCSF, EPO, hGH, or insulin, etc.

BRIEF DESCRIPTION OF THE DRAWINGS

The invention is now described in the following examples, with reference to the following figures in which:

FIG. 1 is a diagram of dual origin vectors;

FIG. 5 shows relative product accumulation with varying induction profiles;

FIG. 6a is a western blot showing the different Fab' species obtained (a) under reducing conditions and (b) under non-reducing conditions; and FIG. 6b is a western blot showing the different Fab' species obtained under non-reducing conditions;

| lane | extract at |
| --- | --- |
| 1 | 4° C. |
| 2 | 30° C. |
| 3 | 43° C. |
| 4 | 44° C. |
| 5 | 46° C. |
| 6 | 4° C. |
| 7 | 30° C. |
| 8 | 43° C. |
| 9 | 44° C. |
| 10 | 46° C. |

Figure 9A:
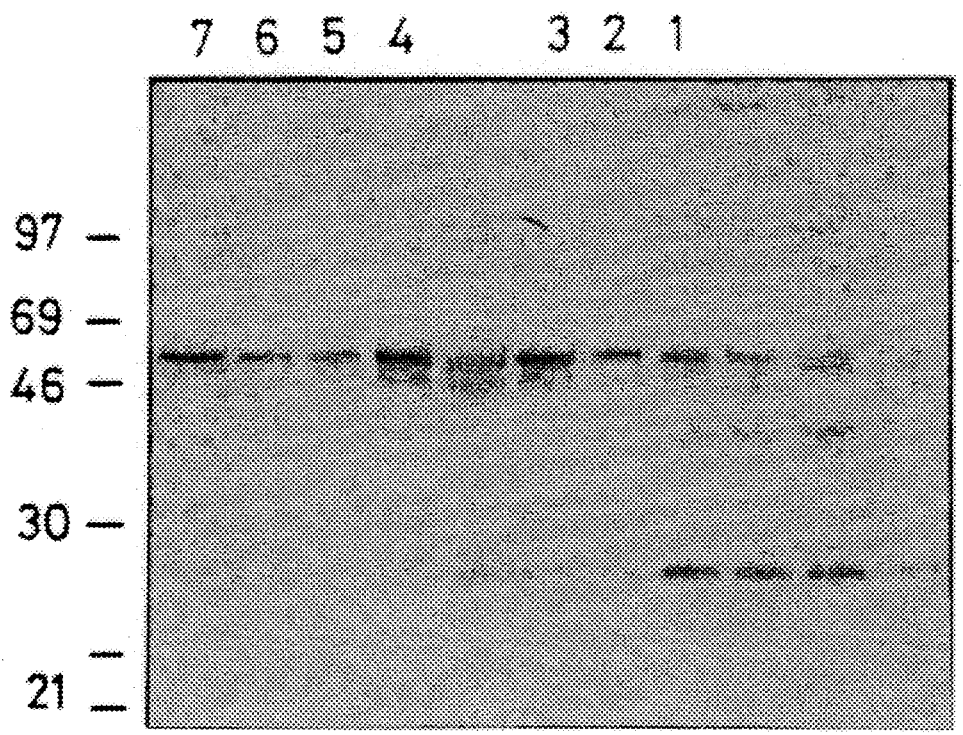

FIG. 9(a) shows western immunoblots of cell extracts
lane 1: A33 humanised Fab' extraction at 30° C.
lane 2: A33 humanized Fab' extraction at 46° C.
lanes 3-7 show cell lysates prepared by lysosyme treatment of cell pellets post incubation at 46° C.

(b) shows western immunoblots of cell extracts
lane 1 A5B7 humanised Fab' extraction at 30° C.
lane 2 A5B7 humanized Fab' extraction at 46° C.

(c) A5B7 humanised Fab'
lanes 1-7 show extracts made by lysosyme lysis post heat treatment at 46° C.

FIG. 10 shows western immunoblot of cell extracts made at 30° C. (lanes 1-8) and 46° C. (lanes 10-17).

Figure 11:
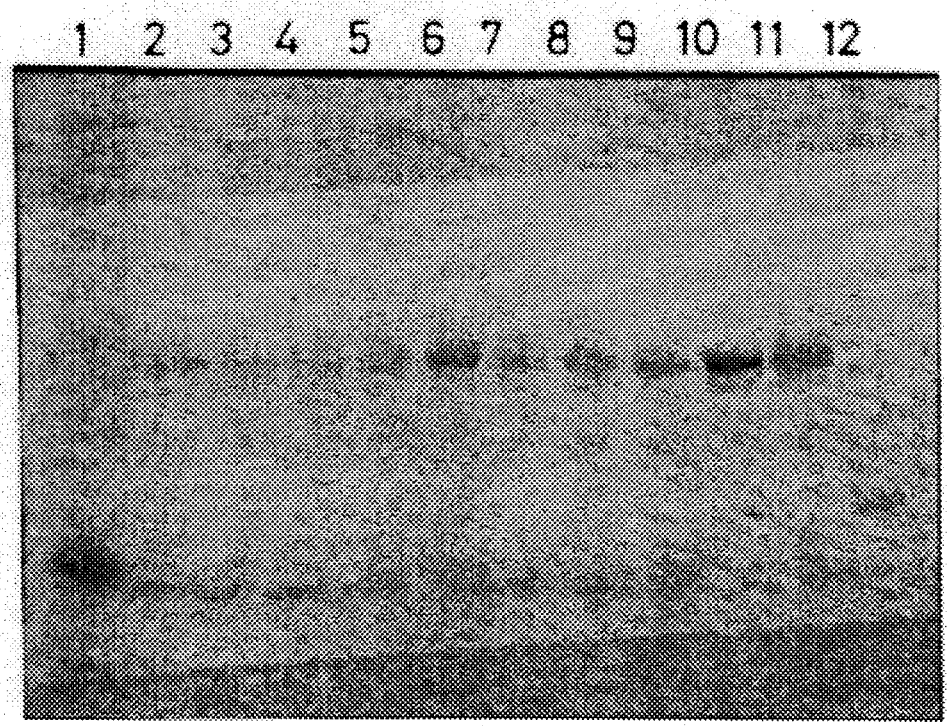

FIG. 11 shows western immunoblot of cell lysates prepared by breaking in a French pressure cell. The extract was then incubated at either 40° C. or 46° C. Samples were taken at regular time intervals and stored on ice. Lanes 1-6 incubation at 40° C. Lanes 7-11 incubation at 46° C.

FIG. 12a shows SDS PAGE anaylsis of Fab' samples extracted from cells by Tris/EDTA treatment and purified by prosepA affinity chromatography. The samples were not heat treated.

FIG. 12b shows SDS PAGE analysis of a Fab' sample extracted from cells by Tris/EDTA treatment and purified by prosepA affinity chromatography. The sample was heat treated.

Figure 12C:

FIG. 12(c) shows SDS PAGE analysis of Fab' samples extracted by lysosyme lysis of cells and purified by prosepA affinity chromatography.

lane 1 non heat treated sample
lane 2 heat treated sample

Figure 13:
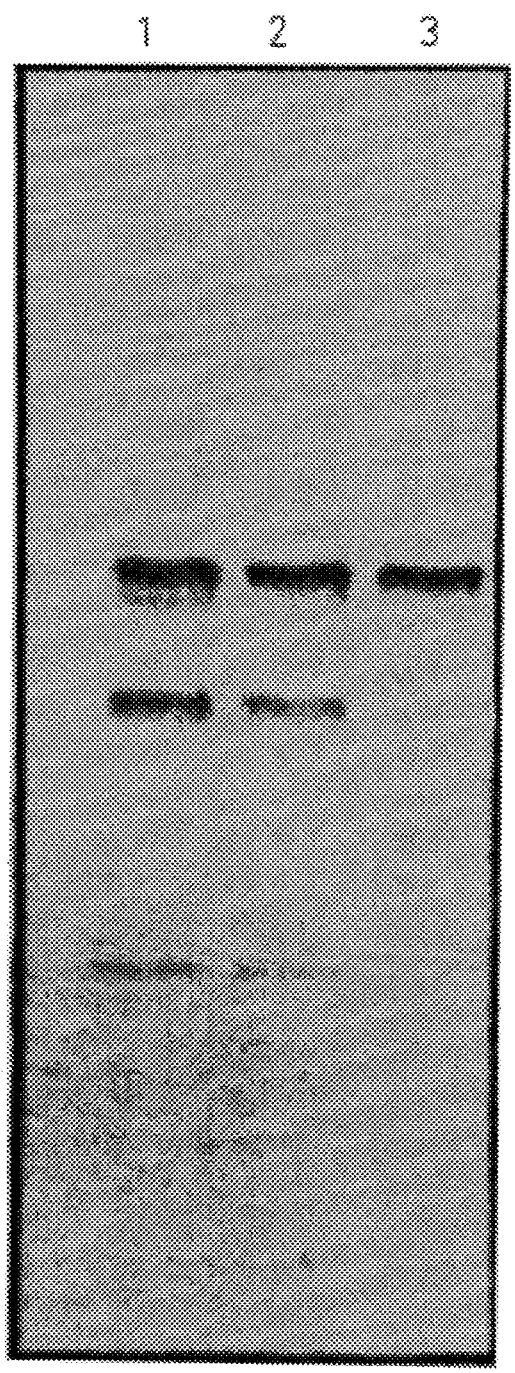

FIG. 13 is a Western immunoblot of prosepA purified Fab' from a preparation not subjected to heat treatment prior to purification.

lane 1 unincubated Fab' prep
lane 2 Fab' prep incubated alone at 46° C. for 12 h
lane 3 Fab' prep incubated at 46° C. for 12 h in the presence of phenyl sepharose.

DETAILED DESCRIPTION OF EMBODIMENTS OF THE INVENTION

CONSTRUCTION OF HEAVY AND LIGHT-CHAIN FUSIONS

A5B7 heavy and light chain sequences cLc (chimeric light chain) and cFd' (chimeric Fd' heavy chain fragment) were isolated as described in International patent application WO 92/01059. These were fused to the E. coli secretion sequence omp A and termed ompA-cLc and ompA-cFd', as described in International patent application WO 92/01059. The sequences were inserted into pSK (Stratagene) as described in WO 92/01059 to produce pSKompA-cLc and pSKompA-cFd'.

pMRR026 was constructed by removing the DNA sequence coding for ompA-cLc as an Xho I-Sma I fragment from pSKompA-cLc, and inserting it into pSP73 (promega Corp.) at the Sal I and Pvu 2 sites. pMRR027 was constructed as described in WO 92/01059.

pAM1 (see FIG. 1) is a dual origin vector which replicates at low copy number using the pSC101 replication functions at 30° C. (Wright et al., Op. Cit.). At this temperature the colE1 replication functions, under the control of the lambda pR promoter, are tightly controlled by the cI 857 repressor, and the target gene under the control of the trp promoter is tightly controlled by the chromosomal trpR repressor. Because the cI857 repressor is temperature sensitive increasing the temperature to above 37° C. leads to amplification of copy number from approximately 5/cell to several hundreds/cell. This amplification titrates out the trp repressor, reducing the relative concentration thereof below a level effective to cause repression, and results in high level expression of the target gene. To construct a pAM1 derivative expressing the A5B7 chimeric Fab' the ompA-cLc and ompA-cFd' fusions were each first cloned as XhoI-EcoRI fragments from pSKompA-cLc and pSKompA-cFd' into the Sal1-EcoR1 gap of pAM1, to give plasmids pMRR030 and pMRR031. The EcorI fragment of pMRR027 carrying ompa-cFd' was then cloned into the EcoRI site of pMRR030 to give pMRR032 (see FIG. 1) with the order trp promoter-cLc-cFd'. Similarly the EcoRI fragment of pMRR026 carrying the ompA-cLc was cloned into EcoRI site of pMRR031 to give plasmid pMRR033, with the order trp promoter-cFd'-cLc.

pMRR032 and pMRR033 were transformed into strains XL1 Blue and W3110 for expression studies in shake flasks and fermenters. Initial shake flask experiments on strains carrying pMRR033 suggested that this plasmid, like the other plasmids with this gene order, were structurally unstable, and no further expression experiments were performed on them (see FIGS. 2 and 3).

Figure 2:
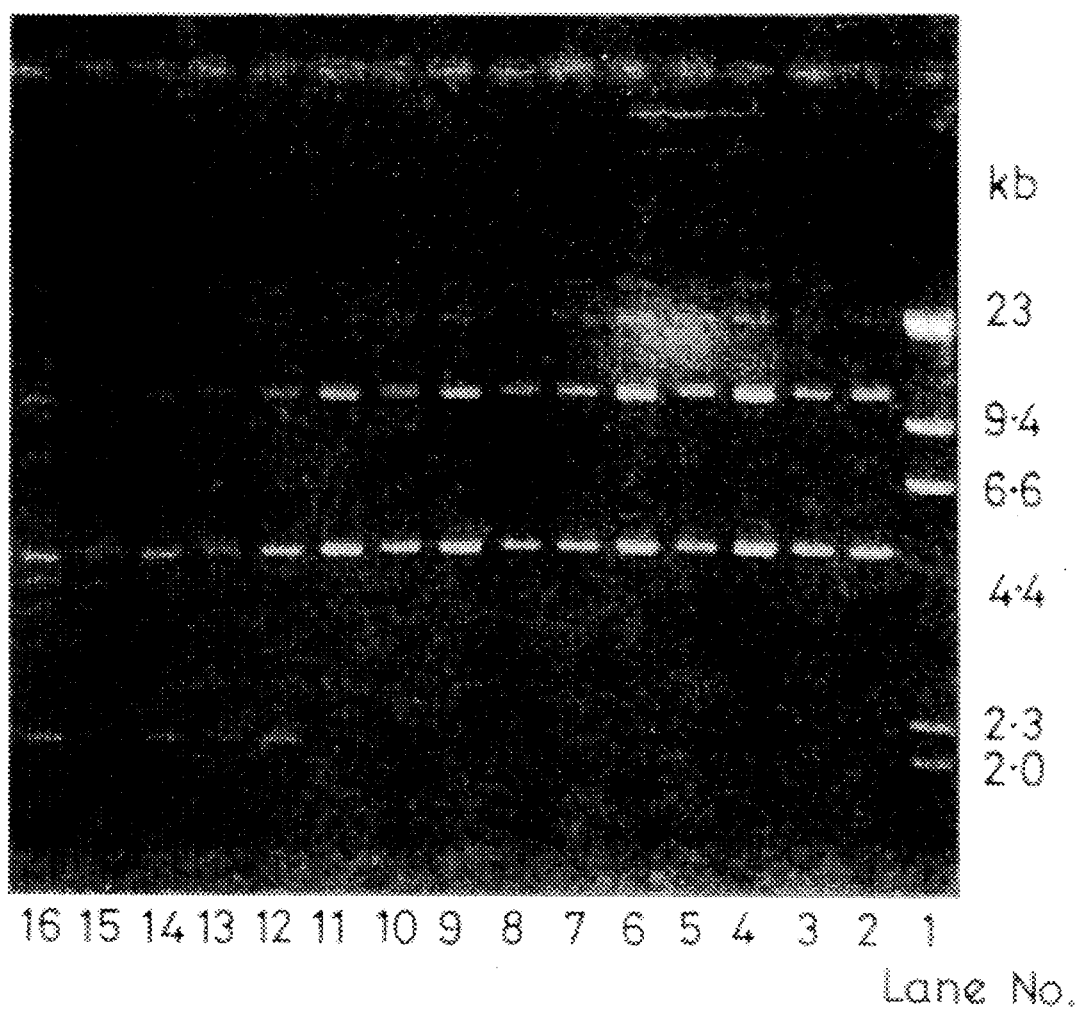
FIG. 2 is a photograph of an agarose gel electrophoresis experiment of plasmid preparations derived from bacterial cultures transfected with plasmids comprising heavy and light chain genes in the orders cLc-cFd' and cFd'-cLc.

FIG. 2 is an agarose gel showing preparations of pQ9Kan-cLc-cFd' and pQ9Kan-cFd'-cLc plasmids.

lane 1: λ-Hind III markers;

lanes 2 to 11: plasmid preparations from strain W3110 transformed with pQ9Kan-cLc-cFd' (A5B7);

lanes 12 to 16: plasmid preparations from strain W3110 transformed with pQ9Kan-cFd'-cLc (A5B7).

In lanes 2 to 11, the intact plasmid can be seen just above the 4.4 Kb marker and no degradation products are apparent.

In lanes 12 to 16, on the other hand, degradation products may be seen at about 2.1 and 4 Kb.

Figure 3:
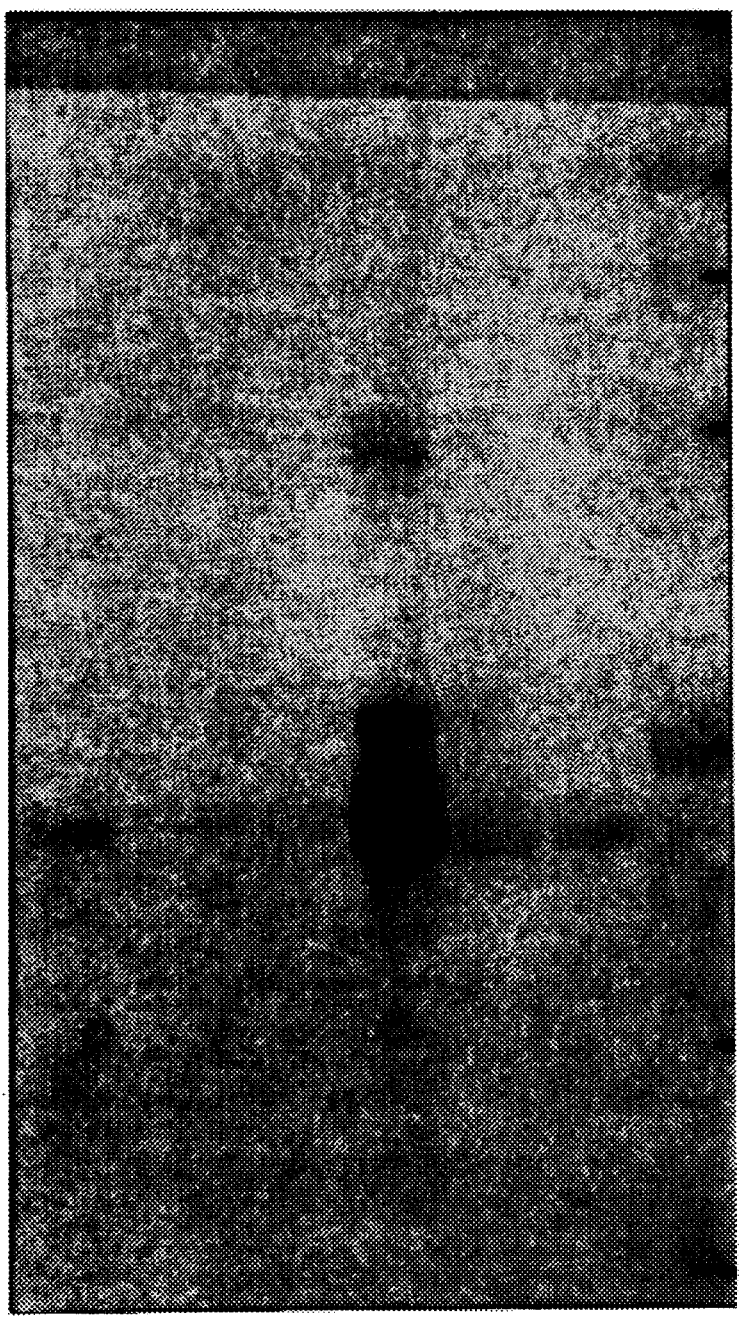
FIG. 3 is a photograph of a western blot which compares the yields of antibody product from DUOV vectors transfected with cLc-cFd' and cFd'-cLc gene constructs.

FIG. 3 is a Western blot of culture supernatants and cell extracts from cell lines transformed with DUOV vectors transformed with cLc-cFd' and cFd'-cLc genes.

lane 12: culture supernatant of XL1B transfected with pMRR032 (cLc-cFd');

lanes 13 and 14: culture supernatants of XL1B transfected with pMRR033 (cFd'-cLc).

lane 15: cell extract of XL1B transfected with pMRR032;

lanes 16 and 17: cell extract of XL1B transfected with pMRR033.

The cLc-cFd' gene order can be seen to give much higher yields of product.

Because previous studies with the dual origin vector had suggested that the exact induction temperature is crucial inductions were carried out in 1.5 l fermenters on XL1Blue/pMRR032 at both 37° C. and 38° C. to optimise the induction temperature for these plasmids. These two induction temperatures gave significantly different growth profiles and yields. Cultures induced at 37° C. continued to grow post induction for two to three hours longer than those induced at 38° C., with a resultant higher titre of Fab' product appearing in the medium. Fab' yields were again estimated by immunoblotting, this method suggesting the yield at 37° C. to be 5-10 mg/l.

Figure 4:
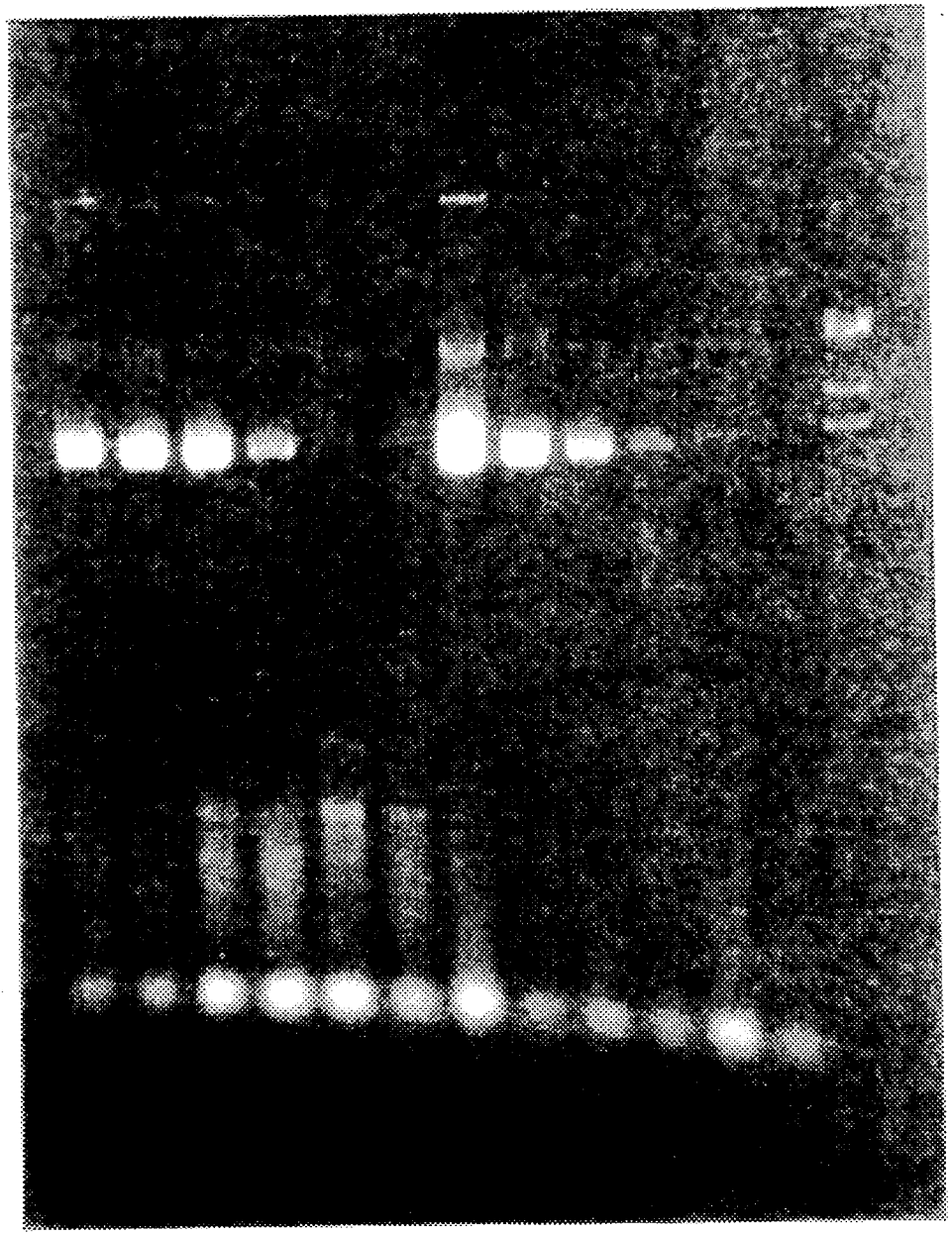
FIG. 4 shows the comparative induction profiles of a dual origin vector at 37° C. and 38° C.

FIG. 4 shows the relative amounts of pMRR032 DNA in samples through these fermentations. It suggests that induction at 38° C. resulted in a rapid increase in plasmid copy number to an approximately constant value while induction at 37° C. gives a slower but more prolonged increase in plasmid copy number which eventually exceeds the plateau observed at 38° C.

FIG. 4 is an agarose gel of plasmid DNA prepared from cell samples from fermentations of XL1 Blue (pMRR032) induced at 37° C. or 38° C.

In FIG. 4 lane identification is as follows:

lane 1 λ Hind III markers lanes 2–7 samples taken 10, 11, 13, 14, 16 and 17 hours after induction at 37° C.

lanes 8–13 samples taken 10, 11, 13, 14, 16 and 17 hours after induction at 38° C.

FERMENTATION PROCESS DEVELOPMENT USING CHIMERIC A5B7 Fab'

Temperature for induction, time at induction temperature before return to 30° C., temperature ramp to induction and complex nitrogen feed were all varied. Product titres were assessed by CEA-binding ELISAs on the crude culture supernatants, with the results shown in FIG. 5. Amplification of copy number in defined medium proved to be lower than previously observed for complex medium but was nevertheless sufficient to support the maximum rate of product accumulation. Fermentations induced at 37° C. or 38° C. and maintained at these temperatures for one hour accumulated more product than those induced at higher temperatures or for longer periods. With these short inductions at 37° C. product continued to accumulate up to the point of harvest, 20 hours after induction. The other fermentation profiles gave shorter product accumulation phases. The data are consistent with the view that maximum yield will result from partial induction to give a relatively low but sustainable level of expression compatible with the maximum rate of translocation, signal cleavage or maintenance of an unfolded conformation in the cytoplasm.

The Fab' product appearing in the culture supernatants gave four major bands on non-reducing PAGE immunoblotted with a polyclonal anti-human Fab antibody (FIG. 6). FIG. 6 shows an SDS-PAGE immunoblot of E. coli W3110 (pMRR032) cultured supernatants. Crude culture supernatant samples were run on a 12% polyacrylamide gel and probed with an anti-human IgG Fab' polyclonal-HRP conjugate. On reducing PAGE the cross-reacting material appeared as a single band with the same mobility as A5B7 Fab' made in mammalian cells. Different fermentations, but not different time of harvesting, were found to give different relative proportions of the four bands. Induction and subsequent growth till harvesting at 37° C. gave a predominance of the correctly assembled Fab' (see FIG. 7).

Figure 7:
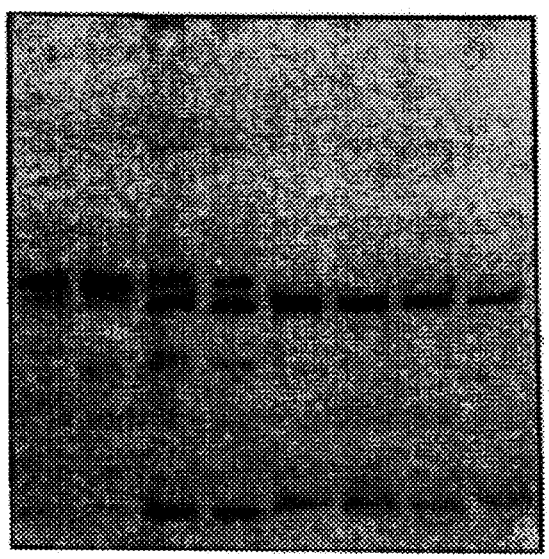
FIG. 7 is a western blot comprising the quantity of correctly folded Fab' obtained by various methods.

In FIG. 7 samples were electrophoresed on a 12% non-reducing polyacrylamide gel then probed with an anti-human IgG Fab' polyclonal-HRP conjugate.

lanes: 1–2 pMRR32 (cA5B7 Fab' in d.o.v.) induced and maintained at 37° C.;

lanes 3–4 pMRR028 (cA5B7 Fab' in pACtac);

lanes 5–6 pMRR044 (gL1gH1 A5B7 Fab' in pACtac);

lanes 7–8 pMRR045 (gL1gH2 A5B7 Fab' in pACtac).

All pACtac plasmids were induced with 200 μM IPTG.

PRODUCTION OF ANTIBODY Fab' FRAGMENTS OF SINGLE BANDED QUALITY (AS DETERMINED BY SDS PAGE ELECTROPHORESIS) FROM E. coli EXPRESSION SYSTEMS This invention describes a method for the production of antibody Fab' fragments largely free from contamination by partially degraded Fab' and free heavy or light chains. The method comprises the use of an elevated temperature phase during the induction stage of the fermentation. The work described here demonstrates that the elevated temperature phase may be used after harvesting the fermentation during an extraction phase and results in similar single banded quality product.

It is reported widely in the literature that, in general terms, lower culture temperatures favour the production of soluble, correctly folded rec DNA products in *E. coli*. Therefore, by delaying the period of elevated temperature to the product extraction and recovery phases the fermentation may be carried out under conditions which are optimised for production of active Fab'. The partially degraded Fab' and free light and heavy chains which accumulate under such conditions may be removed as described above by heat treatment after the fermentation.

The production of multibanded Fab' consisting of intact correctly assembled Fab', two predominant degradation products and free light and heavy chains has been observed in:

Two separate expression hosts

At least 4 separate Fab' fragments

Fermentations using two different plasmids and induction systems

Therefore it appears that this problem is not restricted to an individual expression system or protein.

Figure 8:
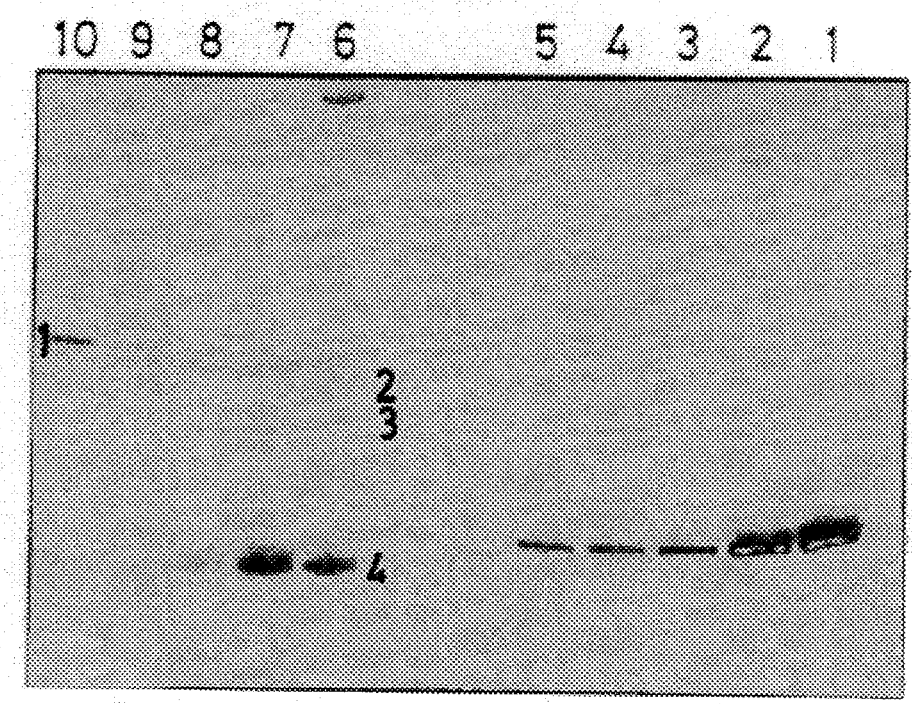
FIG. 8 shows a western immunoblot of cell extracts after incubation overnight at a range of temperatures.

The choice of 46° C. as the incubation temperature for the production of single banded Fab' from a cell extract containing multibanded Fab' was made by testing a range of temperatures up to 46° C. The material produced after incubation at 46° C. was the highest quality. Temperatures above 46° C. were not tested. A western immunoblot of cell extracts incubated at a range of temperatures up to 46° C. is shown in FIG. 8, the samples were run reduced and non reduced to reveal the range of assembled and partially degraded Fab'. This set of extractions was prepared by incubating the intact cells overnight in Tris HCl buffer 100 mM pH 7.4 containing EDTA 10 mM.

FIG. 8 shows a western immunoblot of cell extracts of humanised A33 Fab' produced by resuspending cells harvested by centrifugation in Tris HCl buffer pH 7.4 100 mM containing 10 mM EDTA and incubating overnight at a range of temperatures.

lanes 1–5 samples were reduced with 2MCE lanes 6–10 were run non-reduced.

lanes 1 and 6 were loaded with an extraction made at 4° C., 2 and 7 at 30° C., 3 and 8 at 43° C., 4 and 9 at 44° C. and lanes 5 and 10 at 46° C.

The bands labeled on the non-reduced side are:

| | |
|---|---|
| 1 | Assembled intact Fab' |
| 2 and 3 | Partially degraded Fab' |
| 4 | Intact heavy and light chains |

The titre of protein obtained in the 5 extracts was determined by a dye binding assay kit (Pierce) and found to be 1.06, 0.7, 0.66, 0.28 and 0.26 g/l for extracts made at 4°, 30°, 43°, 44° and 46° C. respectively. Therefore, while the quality of the Fab' material found in the extracts improved with temperature the total protein in the extract was reduced by a factor of up to 4.

Range of fragments to which temperature treatment is applicable.

Extracts made from cells expressing humanised A33 Fab' and those made from cells expressing humanised and chimeric A5B7 Fab' have been shown to contain Fab' predominantly of the assembled intact molecular weight post heat treatment. Prior to heat treatment these extracts contained four main bands of similar intensity when visualised on a Western immunoblot.

Shown in FIG. 9 are extraction samples of A5B7 and A33 humanised Fab' expressed in *E. coli* strain W3110. The extractions were made with and without heat treatment at 46° C.

Humanised A33 Fab' may be constructed and expressed in *E. coli* as described in British patent application number 9225853.2 filed 10th Dec. 1992 and initial British patent application filed on even date herewith (ref. PA 345).

Heat treatment of periplasmic extracts and cell lysates.

The cell extracts described above were made by incubating cells in buffer containing EDTA (10 mM) and resulted in a selective release of periplasmic proteins. Cell lysis by enzymatic or mechanical means was found to release more active Fab' than any selective extraction system. The unheated cell lysates were found to contain similar profiles of Fab and degradation products to those found in Tris HCl/EDTA extracts. Cell lysates could be heat treated to remove the partially degraded Fab and free heavy and light chain found in the soluble fraction. The heat treatment phase could be used pre or post breakage/lysis with similar affect. Shown in FIG. 9 are samples of cell extracts post heat treatment, these samples show that the Fab' is predominantly in the assembled intact form.

FIG. 9 shows Western immunoblots of cell extracts made by incubation in Tris/EDTA buffer.

FIG. 9a shows A33 humanised Fab'.

lane 1 extraction made at 30° C.

lane 2 extraction made at 46° C.

lane 3–7 show cell lysates prepared by lysozyme treatment of cell pellets post incubation at 46° C.

Figure 9B:
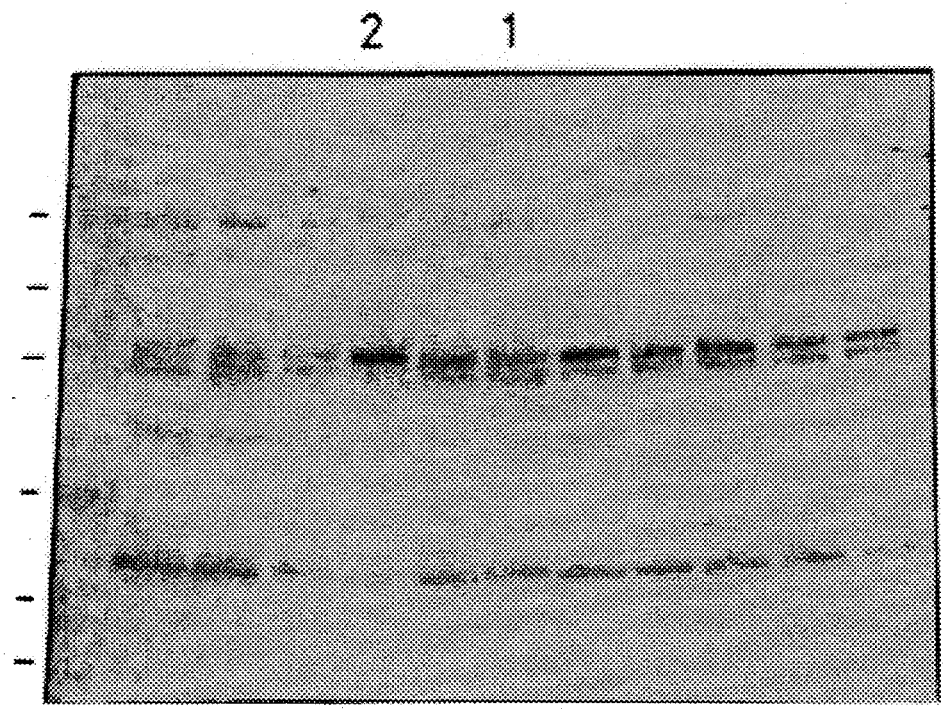

FIG. 9b shows A5B7 humanised Fab' lane 1 extraction made at 30° C.

lane 2 extraction made at 46° C.

Figure 9C:
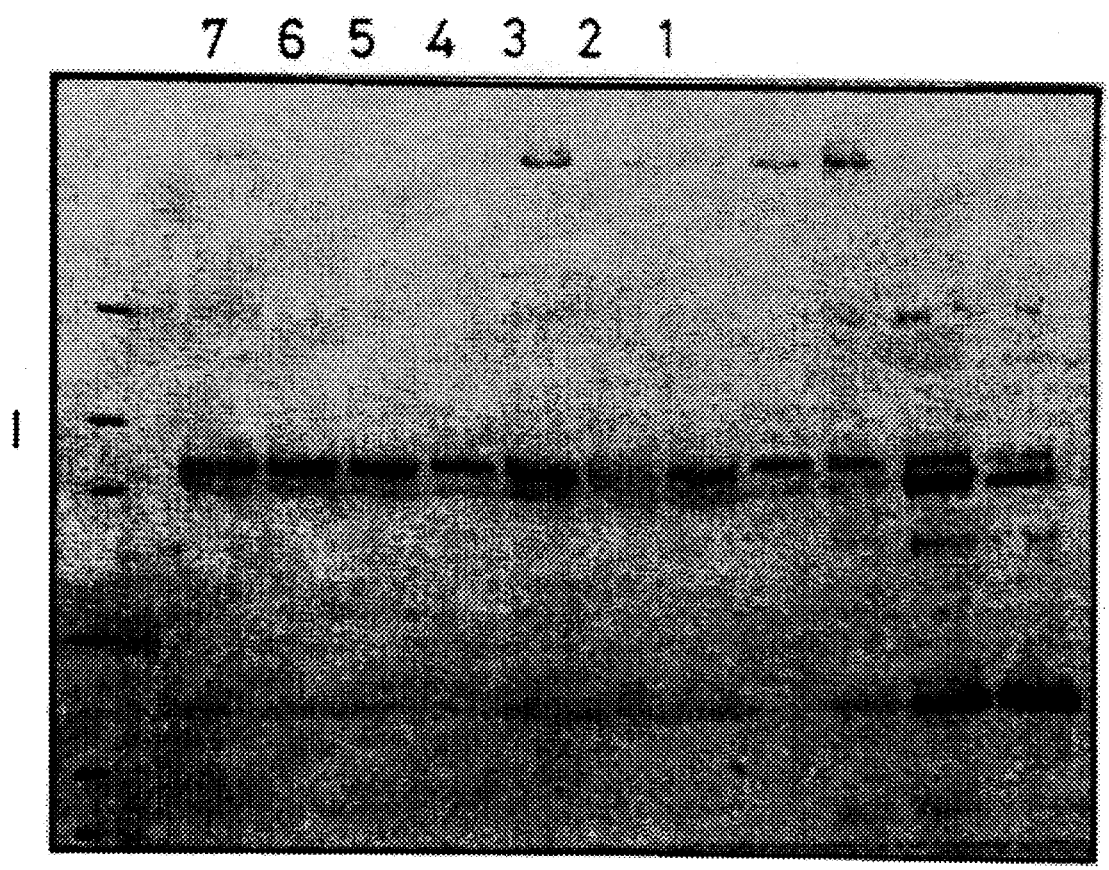

FIG. 9c shows A5B7 humanised Fab' lanes 1–7 show extracts made by lysozyme lysis post heat treatment at 46° C.

Heat treatment of cell pellets sampled at regular intervals during a fermentation FIG. 10 shows a western immunoblot of cell extracts made by incubation in Tris HCl/EDTA buffer at 30° C. (lanes 1–8) and 46° C. (lanes 10–17). The samples loaded represent a time course across a fermentation expressing humanised A33 Fab'.

Predominantly single banded material is shown in the samples extracted at 46° C. and 4 principal bands are shown in the samples extracted at 30° C. Therefore, the partially degraded Fab' and free light and heavy chains were found to be present when Fab' was first detected in the periplasmic extract and samples taken throughout the fermentation could be converted to the predominantly single banded form.

Time course of heat treatment at 46° C.

Experiments were carried out to determine the incubation periods at 46° C. required to obtain predominantly intact single banded Fab' from a mixture of degradation products, intact Fab' and free light and heavy chain. These experiments tested two procedures:

1. The intact cells were incubated at 46° C. with samples being removed at appropriate intervals and stored on ice. All samples were then lysed and analysed by western immunoblotting and activity ELISA.

2. An aliquot of cell suspension was lysed then incubated at 46° C. Samples were taken at appropriate time intervals and analysed by western immunoblotting and activity ELISA.

Analysis of the samples by western immunoblotting

The quality of material as determined by Western immunoblotting was found to be best in the 20 h incubation sample at 40° C. and in the 10 h sample taken from the 46° C. incubation. The western immunoblot (FIG. 11) shows no evidence of loss of the intact Fab' during either incubation, indeed the final samples show a clearer more intense Fab' band. This apparent increase in Fab' may be an artifact resulting from more efficient transfer of the protein during blotting in the later samples which are known to contain less total protein. The ELISA results, in contrast to the western immunoblot, show a reduction in titre of material binding to the antigen on the solid phase. This may have resulted from some of the incorrectly assembled or partially degraded Fab' binding to the antigen and being detected in the assay.

FIG. 11 shows a Western immunoblot of cell lysates (expressing humanised A33 Fab') prepared by breaking in a French pressure cell. The extract was then incubated at either 40° C. or 46° C. Samples were taken at regular time intervals and stored on ice. Lanes 1–6 incubation at 40° C. Lanes 7–11 incubation at 46° C.

Recovery of Fab' proteins by Protein A purification pre and post heat treatment

The pattern of intact Fab', degradation products and free heavy and light chains visualised by western blotting of samples pre and post heat treatment was found to be similar to that recovered by protein A purification and analysis of column eluates by SDS PAGE and coomassie blue staining. Preparations of predominantly intact single banded Fab' from initial starting mixtures of Fab', degraded Fab' and free heavy and light chains were obtained from both Tris HCl/EDTA periplasmic extracts and cell lysates. Shown in FIGS. 12(a)–(c) are samples of periplasmic extracts and cell lysates (expressing humanised A33 Fab') with and with and without heat treatment (FIGS. 12(a)–(c) lanes 1 to 5 periplasmic extracts non heat treated and lane 6 heat treated, FIG. 12(c) lane 1 cell lysate non heat treated and lane 2 heat treated).

FIG. 12a shows SDS PAGE gels of Fab' samples extracted from cells by Tris/EDTA treatment and purified by prosepA affinity chromatography.

lanes 1–5 non-heat treated lane 6 heat treated.

FIG. 12(c) shows SDS PAGE gel of Fab' samples extracted by lysozyme lysis of cells and purified by prosepA affinity chromatography.

lane 1 non heat treated lane 2 heat treated.

Recovery of Single Banded Fab from Purified Material Containing Partially Degraded Fab and Free Heavy and Light Chain Material purified from cultures which had not been subjected to heat treatment has been shown to consist of four principal Fab associated bands. Single banded (correctly assembled and intact) material may be recovered from purified four banded material by incubation at 46° C. in the presence of Phenyl Sepharose. The partially purified material is in a solution of a citrate buffer pH2 in which the pH has been raised to pH7 by the addition of Tris.

FIG. 13 shows a Western immunoblot of prosepA purified humanised A5B7 Fab' from a preparation not subjected to heat treatment prior to purification.

lane 1 unincubated Fab' prep lane 2 Fab' prep incubated alone at 46° C. for 12 h.

lane 3 Fab' prep incubated at 46° C. for 12 h in the presence of phenyl sepharose.

The invention is described above by way of example only, and numerous modifications of detail will be apparent to those skilled in the art which fall within the scope of the appended claims.

METHODS FOR THE EXPRESSION OF ANTIBODY FRAGMENTS IN *E. coli* USING THE DUAL ORIGIN AND pAC tac EXPRESSION VECTORS 1. Storage of Strains
2. Revival of Cultures and Inoculum Preparation
3. Media
4. Shake Flask Culture and Induction Procedures
   4.1 Host strain W3110 with pAC tac vector
   4.2 Host strain W3110 with dual origin vector
5. Fermentor Culture and Induction Procedures
   5.1 Host strain W3110 with pAC tac vector
   5.2 Host strain W3110 with dual origin vector
6. Periplasmic Extraction Procedures

1. STORAGE OF STRAINS

A single colony from a freshly transformed plate was streaked out on an LA plate containing the appropriate antibiotic selection. A single colony from this plate was used to inoculate a 250 ml Edenmeyer flask containing 40 ml LB medium+appropriate antibiotic selection (dual origin vector: ampicillin, pAC tac vector: chloramphenicol). This flask was incubated at 30° C. and 250 RPM in an orbital incubator until the culture reached an optical density (OD 600 nm) of 2 (mid exponential growth phase) taking approximately 8 h to reach this point.

Aliquots (750 µl) of this culture were mixed with 250 µl sterile glycerol solution (50% v/v in $H_2O$) in a 2 ml sterile ampoule (Sterlin). These glycerol stocks were stored at −70° C. without controlling freezing rate.

2. REVIVAL OF STRAINs AND INOCULUM PREPARATION

Inocula for all experiments were prepared from frozen glycerol stocks in LB medium containing Cm or Amp as appropriate, the seeding density was usually 300 µl glycerol stock per litre LB. Inoculum cultures, grown in Edenmeyer flasks (1 L containing 200 ml medium) incubated at 30° C. and 250 RPM in an orbital shaker were used when an OD 600 nm of 3 had been attained (normally 12–16 h). Fermentors and shake flasks were seeded with 5–10% volumes of inoculum.

3. MEDIA 3.1 LA: Luria Agar
LA Cm: LA+chloramphenicol 25 µg/ml
LA Amp: LA+ampicillin 25 µg/ml 3.2 LB: Luria Broth
LB Cm and LB Amp both 25 µg/ml 3.3 YEGLY

| Component | g/L |
| --- | --- |
| Glycerol | 20.0 |
| $(NH_4)_2SO_4$ | 7.0 |
| $NaH_2PO_4.2H_2O$ | 6.24 |
| Yeast extract (Difco) | 40.0 |
| SM6 trace elements | 10 ml/L |
| Antifoam solution (1)% mazu DF843) | 1 ml/L |

This formulation was made up to 1 L with deionised water, 3.4 SM6

| Component | g/L |
| --- | --- |
| $(NH_4)_2SO_4$ | 5 |
| $NaH_2PO_4$ | 6.24 |
| Trace element solution (SM6) | 10 ml/L |
| Antifoam solution (10% mazu DF843) | 1 ml/L |

This formulation was made up to 0.96 L with deionised water, Where the carbon source used was glycerol this was added to a concentration of 20 g/L prior to autoclaving. Where glucose and or lactose were used these were added post sterilisation as 50% solutions (sterilised by autoclaving) to final concentrations of 20 g/L.

SM6 Trace element solution

| Component | g/L 100x stock solution |
|---|---|
| NaOH | 15.0 |
| EDTA | 60.0 |
| $MgSO_4.7H_2O$ | 20.0 |
| $CaCl_2.6H_2O$ | 5.0 |
| $ZnSO_4.4H_2O$ | 2.0 |
| $MnSO_4.4H_2O$ | 2.0 |
| $CuSO_4.5H_2O$ | 0.5 |
| $CoCl_2.6H_2O$ | 0.095 |
| $FeSO_4.7H_2O$ | 10.0 |
| $H_3BO_3$ | 0.031 |
| $Na_2MoO_4$ | 0.002 |

Each component was dissolved individually in deionised water and added to the bulk solution in the sequence shown to a final volume of 1 L.

3.5 SM6A

| Component | g/L |
|---|---|
| $(NH_4)SO_4$ | 5.0 |
| $NaH_2PO_4$ | 6.24 |
| KCl | 3.87 |
| $MgSO_4.1H_2O$ | 0.56 |
| Citrate | 4.0 |
| SM6A Trace Element solution | 10 ml/L |
| Antifoam (Mazu DF843 10% in $H_2O$) | 1.0 ml/L |

Made up to 0.95 L with deionised water.
SM6A Trace element solution

| Component | g/L 100x stock solution |
|---|---|
| Citrate | 100.0 |
| $CaCl_2.6H_2O$ | 5.0 |
| $ZnSO_4.4H_2O$ | 2.0 |
| $MnSO_4.4H_2O$ | 2.0 |
| $CuSO_4.5H_2O$ | 0.5 |
| $CoSO_4.6H_2O$ | 0.4 |
| $FeCl_3.6H_2O$ | 9.67 |
| $H_3BO_3$ | 0.03 |
| $NaMoO_4$ | 0.02 |
| KCl | 74.5 |

Made up to 1 l with deionised water. Components were added in the order shown and were allowed to dissolve completely prior to the addition of the next salt.

Defined media were brought to pH 6.95 using 3.6M $NH_4OH$ after autoclaving.

Carbon sources for defined media were as described in the fermentation methods section.

All media were sterilised by autoclaving at 121° C. for 20 min.

Glucose and Lactose were autoclaved separately as 50% solutions (w/v) in $H_2O$ and added to cultures as described in the fermentation methods section. Prior to autoclaving, conc $H_2SO_4$ (100 μl per litre) was added to glucose solutions.

Glycerol for feeding during fermentations was autoclaved neat or as a 50% w/v solution in $H_2O$.

Casamino acids (Difco, 200 g/l solution in $H_2O$ sterilised by autoclaving) were added to give a final concentration of 20 g/L where described.

4. SHAKE FLASK CULTURE AND INDUCTION PROCEDURES 4.1 Host Strain W3110 with pAC tac Expression Vector Shake flask cultures were made in 250 ml Erlenmeyer baffled flasks containing 40 ml YEGLY medium seeded with 4 ml inoculum prepared as described in section 2. Cultures were incubated at 30° C. and 250 RPM in an orbital incubator. Induction of product expression was obtained at OD 600 nm=5 by adding a 40 μl aliquot of IPTG (200 mM, freshly prepared aqueous solution sterilised by filtration). Cultures induced at an OD 600 of 2.5 produced higher yields for certain fragments than those induced at 5. Addition of IPTG to cultures which had reached OD's of 6 or greater and had moved into the decline phase of growth did not induce product expression.

Culture supernatants were harvested by centrifugation 12 h post induction with IPTG.

4.2 Host Strain W3110 with the Dual Origin Expression Vector

Cultures were grown as described in Section 4.1. Induction of product expression was achieved by transferring flasks to an orbital incubator pre equilibrated at 40° C. when cultures had reached an OD of 5.

Culture supernatants were harvested by centrifugation 12 h post induction by temperature switching.

5. FERMENTOR CULTURE AND INDUCTION PROCEDURES 5.1 Host Strain W3110 with pAC tac Expression Vector 5.1.1 Complex medium fermentations Fermentations were made in YEGLY medium inoculated at a seeding density of 5% with the culture described in section 1. The culture pH was controlled at 7.0±0.05 by addition of 2M NaOH or 2M $H_2SO_4$. Temperature was maintained at 30° C. and dissolved oxygen tension (DOT) was controlled at a value >10% air saturation by automatic control of agitator speed. Aeration was set at 0.75 v/v/min. Oxygen utilisation rates and carbon dioxide evolution rates were determined from exhaust gas analysis performed by mass spectrometry. Product formation was induced by adding IPTG as a filter sterilised 1000× stock solution to a final concentration of 200 μM when the culture OD had reached 5.

Fermentations were run with and without chloramphenicol (25 μg/ml), no requirement for antibiotic selection in the fermentation medium has been demonstrated.

Culture supernatants were harvested 12 h post induction by centrifugation 4200 RPM rmax 240 mm (1–2 l fermentations) or by tangential flow filtration (15 l and 150 l fermentations). Clarification of broths was superior with tangential flow filtration (TFF).

5.1.2 Defined Medium Fermentations

Fermentations were made in medium SM6 or SM6A, glucose was used as the initial carbon and energy source for all fermentations and was added after medium sterilisation to a concentration of 20 g/l. Culture pH was brought to and maintained at 6.95 by the addition of 3.6M $NH_4OH$, or 2M $H_2SO_4$. DOT was maintained above 10% by control of agitator speed, culture temperature was maintained at 30° C. throughout the fermentation.

IPTG inductions: Cultures were induced with IPTG (final concentration 200 μM) at OD 600 nm=40. Cultures induced with IPTG were fed glucose as required, (either in response to OUR or as predicted by an approximate yield of 1 OD/g glucose/l).

Lactose inductions: Induction of product expression was also obtained by switching the carbon source to lactose from glucose. Glucose was fed to support the culture to an OD of approximately 30 (an accumulative addition of 30 g/l). Lactose feeding was started at an OD of approximately 25, as with glucose, lactose was then fed (normally as individual shots of 50% lactose to a concentration of 10 g/l culture) as required. The 50% lactose solution was held in a water bath at 55° C. after autoclaving to prevent crystallisation.

Cultures induced by IPTG were harvested 20 h post induction. Cultures induced by lactose feeding were harvested 24–30 h after the switch from glucose to lactose utilisation.

Where casamino acids were added to defined medium fermentations these additions were made 3 h post induction.

5.2 Host Strain W3110 with the Dual Origin Expression Vector 5.2.1 Complex medium fermentations These fermentations were made as described in section 5.1.1 except that induction of product formation was achieved by increasing the culture temperature when the OD had reached 20. A temperature switch to 37° C. from 30° C. and holding the culture at 37° C. was used.

5.2.2 Defined medium fermentations

These fermentations were made as described in section 5.1.2 except that glycerol was used throughout as the carbon and energy source (starting concentration 20 g/L). Medium SM6A could only be used with citrate reduced to 1 g/L total.

Fermentations run using glucose as the carbon source resulted in induction of product expression prior to temperature switching and in the absence of plasmid amplification.

Cultures were fed glycerol as required, again in response to the online OUR data or as predicted by an approximate yield of 1 OD/g glycerol/L.

Fermentations were harvested 12 h post temperature induction by centrifugation or TFF. Where inductions did not arrest growth (normally 4–6 h post temperature shift) it was not possible to maintain the DOT above 10% air saturation, these cultures were allowed to become oxygen depleted and harvested.

We claim:

1. A process to facilitate the isolation of soluble, correctly-folded antibody molecules comprising subjecting a preparation comprising soluble, correctly-folded antibody molecules and partially degraded or incorrectly folded antibodies to a step to raise the operating temperature to an elevated temperature within the range of 34° C. to 60° C. in order to facilitate the removal of the partially degraded or incorrectly folded antibodies.

2. A process according to claim 1 wherein the preparation comprising soluble, correctly-folded antibody molecules and partially degraded or incorrectly folded antibodies is the product of a fermentation comprising culturing a host cell transformed with an exression vector which encodes at least part of an antibody light chain and an expression vector encoding at least part of an antibody heavy chain, such that at least some of the light chain and heavy chain molecules are secreted and combine to form soluble, correctly-folded and assembled antibody.

3. A process according to claim 2 wherein said step to raise the operating temperature is carried out at 40° C. to 60° C. for a period of up to 18 hours.

4. A process according to claim 2 wherein the preparation subjected to said step to raise the operating temperature comprises disrupted cells.

5. A process according to claim 2 wherein said step to raise the operating temperature is carried out during the expression phase of the fermentation.

6. A process according to claim 2 wherein the preparation subjected to said step to raise the operating temperature further comprises a batch hydrophobic chromatography matrix.

7. A process according to claim 5 comprising the steps of:
   a) culturing a bacterial cell transformed with at least one expression vector comprising an origin of replication which is inducible from a repressed state at a repressive temperature, at which it replicates at a low copy number, to an induced state at an elevated permissive temperature, at which it replicates at a high copy number, and a DNA coding sequence encoding all or part of an antibody molecule comprising a light chain polypeptide and a heavy chain polypeptide under the control of a promoter which is repressed when the vector is at a low copy number and of a secretion sequence, in a medium at the repressive temperature at which the vector is maintained at a low copy number and recombinant gene expression is not induced;
   b) raising the operating temperature of the culture medium to the elevated permissive temperature to induce replication of the vector to high copy number;
   c) maintaining the operating temperature of the medium at the elevated permissive temperature and
   d) optionally collecting the antibody molecule product expressed into the periplasm of the host cell or the culture medium.

8. A process according to claim 2, wherein said antibody molecule is a natural, humanised or chimeric antibody or a fragment thereof.

9. A process according to claim 2, further comprising the step of isolating the soluble, correctly folded antibody molecules.

10. A process according to claim 7, wherein in steps (b) and (c), said elevated permissive temperature is 40°–60° C.

11. A process according to claim 10, wherein in step (c), said elevated permissive temperature is maintained for a period of 10 to 18 hours.

12. A process according to claim 5, wherein said antibody molecule is a natural, humanised or chimetic antibody or a fragment thereof.

* * * * *